United States Patent [19]

Cereghetti et al.

[11] Patent Number: 5,488,172
[45] Date of Patent: Jan. 30, 1996

[54] CHIRAL PHOSPHORUS COMPOUNDS

[75] Inventors: Marco Cereghetti, Basel, Switzerland; Joseph Foricher, Mulhouse, France; Bernd Heiser, Inzlingen, Germany; Rudolf Schmid, Münchenstein, Switzerland

[73] Assignee: Hoffmann-La Roche Inc., Nutley, N.J.

[21] Appl. No.: 294,895

[22] Filed: Aug. 23, 1994

Related U.S. Application Data

[63] Continuation of Ser. No. 152,932, Nov. 15, 1993, abandoned, which is a continuation of Ser. No. 884,628, May 15, 1992, abandoned, which is a continuation of Ser. No. 521,498, May 10, 1990, abandoned.

[30] Foreign Application Priority Data

May 18, 1989 [CH] Switzerland .............................. 1905/89
Mar. 16, 1990 [CH] Switzerland .............................. 880/90

[51] Int. Cl.⁶ ........................................................ C07F 9/50
[52] U.S. Cl. ................................................................ 568/13
[58] Field of Search .................................................. 568/13

[56] References Cited

U.S. PATENT DOCUMENTS

| | | | |
|---|---|---|---|
| 4,556,740 | 12/1985 | Hansen et al. ............................. | 568/13 |
| 4,764,629 | 8/1988 | Sayo et al. .................................. | 556/23 |
| 4,766,225 | 8/1988 | Sayo et al. .................................. | 556/16 |
| 4,766,227 | 8/1988 | Sayo et al. .................................. | 556/21 |

FOREIGN PATENT DOCUMENTS 0256634 2/1988 European Pat. Off. .
0269395 6/1988 European Pat. Off. .

OTHER PUBLICATIONS

Schmid et al., Helv. Chim. Acta, 74: 370–389 (1991).
Heiser et al., Tetrahedron: Asymmetry, 2: 51–62 (1991).

*Primary Examiner*—Robert W. Ramsuer
*Assistant Examiner*—Michael G. Ambrose
*Attorney, Agent, or Firm*—George M. Gould; William H. Epstein; Bruce A. Pokras

[57] ABSTRACT

Novel chiral phosphorus compounds of the formula

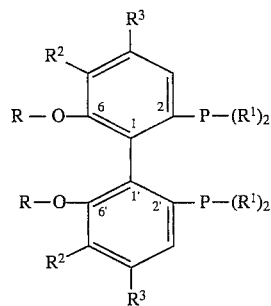

I wherein R signifies lower alkyl, $R^1$ signifies phenyl and $R^2$ and $R^3$ signify hydrogen or lower alkoxy, which are suitable in the form of complexes with a metal of Group VIII as catalysts for asymmetric hydrogenations and for enantioselective hydrogen displacements in prochiral allylic systems.

15 Claims, No Drawings

CHIRAL PHOSPHORUS COMPOUNDS

This is a continuation of application Ser. No. 08/152,932, filed Nov. 15, 1993, which is a continuation of 07/884,628, filed May 15, 1992, which is a continuation of Ser. No. 07/521,498, filed May 10, 1990, all now abandoned.

SUMMARY OF INVENTION

The present invention is concerned with novel chiral phosphorus compounds of the formula

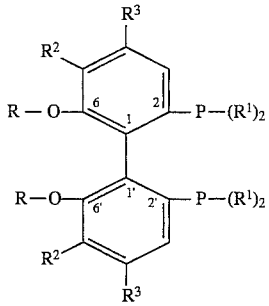

wherein R is lower alkyl; $R^1$ is phenyl or substituted phenyl; and $R^2$ and $R^3$ are hydrogen or lower alkoxy, which compounds have the (R)- or (S)-configuration.

The invention is also concerned with the manufacture of the phosphorus compounds of formula I and with their use for enantioselective reactions such as e.g. asymmetric hydrogenations or also enantioselective hydrogen displacements in prochiral allylic systems.

DETAILED DESCRIPTION

Where $R^1$ is substituted phenyl the phenyl moiety can be substituted in the meta- or para-position or also multiply-substituted with such substituents as lower alkyl, lower alkoxy, etc. Among the substituents, lower alkyl is preferred with methyl being especially preferred. The term "lower alkyl" designates both straight-chain or branched alkyl groups having 1 to 4 carbon atoms such as methyl, ethyl, propyl, isopropyl, n-butyl, isobutyl and tert. butyl. The term "lower alkoxy" designates alkoxy group where lower alkyl is as defined above.

Preferred phosphorus compounds of formula I above are those in which R signifies methyl, $R^1$ signifies unsubstituted phenyl or phenyl which is substituted in the meta- or para-position with methyl and $R^2$ and $R^3$ signify hydrogen or methoxy.

Especially preferred compounds of formula I are:
(R)- or (S)-(6,6'-Dimethoxybiphenyl-2,2'-diyl)bis(diphenylphosphine),
(R)- or (S)-(5,5',6,6'-tetramethoxybiphenyl-2,2'diyl) bis-(diphenylphosphine),
(R)- or (S)-6,6'-dimethoxybiphenyl-2,2'-diyl)bis(di-p-tolylphosphine) and
(R)- or (S)-(4,4',5,5',6,6'-hexamethoxybiphenyl-2,2'-diyl)bis (diphenylphosphine).

The compounds of formula I in accordance with the invention can be manufactured by subjecting a compound of the formula

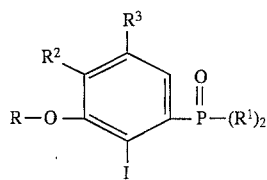

wherein R, $R^1$, $R^2$ and $R^3$ are as above, to an Ullmann coupling, resolving a thus-obtained compound of the formula

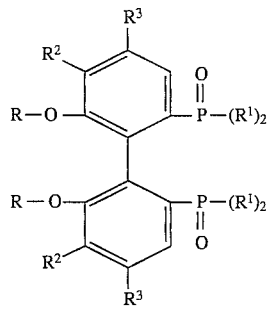

wherein R, $R^1$, $R^2$ and $R^3$ are as above, which is present in the (RS)-form, by means of dibenzoyltartaric acid or di-p-toluoyltartaric acid into the (R)- and (S)-form and subsequently reducing the resolved compound of formula III.

The conversion of a compound of formula II into a compound of formula III, which is present in the (RS)-form, is effected in accordance with the invention by means of an Ullmann coupling. This is a reaction which is known per se and which can be carried out under the usual conditions. Thus, this reaction can be carried out, for example, by heating a compound of formula II in an inert organic solvent such as e.g. N,N-dimethylformamide with e.g. copper powder activated with iodine to a temperature of about 110° C. to about 200° C. If desired, the reaction can also be carried out in the absence of a solvent, i.e. in the molten state.

The compounds of general formula II which are used as starting materials are novel and are accordingly also an object of the present invention. They can be prepared, for example, by subjecting a compound of the formula

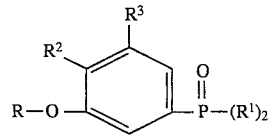

wherein R, $R^1$, $R^2$ and $R^3$ are as above, to an ortho-lithiating/iodinating reaction.

The ortho-lithiation of a compound of formula IV can be effected in a manner known per se. For example, this reaction can be effected by reacting a compound of formula IV with a lithium amide, e.g. lithium diisopropylamide or lithium 2,2,6,6-tetramethylpiperidine in tetrahydrofuran at a temperature below −50° C., preferably at about −78° C. The subsequent iodination can be effected conveniently with molecular iodine, with ICl or IBr, if desired in tetrahydrofuran and, if desired, at a temperature below −50° C.

The compounds of formula IV which are also used hereinbefore as starting materials are known compounds or analogues of known compounds which can be prepared readily in a manner known per se [J. J. Monagle et al., J. Org. Chem. 32, 2477 (1967)].

The racemate resolution of a compound of formula III, which is present in the (RS)-form, by means of (−)- or (+)-dibenzoyltartaric acid (DBT) or (−) or (+)-di-p-toluoyltartaric acid (DTT) can be carried out in a manner known per se for racemate cleavages of phosphine oxides. This is conveniently effected in an inert organic solvent and at a temperature of about 0° C. to about 60° C. As solvents there can be named here, in particular, chloroform, methylene chloride, ethyl acetate, acetone, alcohols such as methanol or ethanol and the like as well as mixtures thereof.

The thus-obtained adducts of the compounds of formula III with (−)- or (+)-DBT or -DTT can subsequently be treated with an inorganic base in a manner known per se, whereby the respective (R)- and, respectively, (S)-form of the compounds of formula III are liberated.

The compounds of formula III, namely not only those in the (RS)-form but also those in the (R)- or (S)-form, are novel compounds and as such are also an object of the present invention.

The reduction of a thus-obtained compound of formula III, which is present in the (R)- or (S)-form, can be carried out in a manner known per se. This can be effected, for example, with silanes such as e.g. trichlorosilane in an aromatic hydrocarbon such as, for example, in boiling xylene or also in acetonitrile etc., conveniently in the presence of an auxiliary base such as, for example, triethylamine or preferably tributylamine. If desired, this reduction can also be carried out in an autoclave under pressure.

If desired, a compound of formula III, which is present in the (RS)-form, can also be reduced, prior to the racemate resolution, into the corresponding (RS)-compound in an analogous manner to the reduction of the corresponding compounds of formula III, which are present in the (R)- or (S)-form. These (RS)-compounds are also novel and are an object of the present invention.

All previously mentioned reactions—with the exception of the racemate resolution—are conveniently carried out under an inert gas such as e.g. argon or nitrogen.

The phosphorus compounds of formula I in accordance with the invention form complexes with metals of Group VIII, especially with ruthenium, rhodium and iridium, which can be used as catalysts in asymmetric hydrogenations and also for enantioselective hydrogen displacements in prochiral allylic systems. Ruthenium complexes are preferred for the aforementioned hydrogenations, while rhodium complexes are preferred for isomerizations. These catalysts, i.e. the complexes from a metal of Group VIII and the phosphorus compounds of formula I, are novel and are also an object of the present invention.

The complexes in question can be produced in a manner known per se, e.g. by reacting a compound of formula I with a compound which can yield a metal of Group VIII in a suitable inert organic or aqueous solvent. As suitable compounds which yield e.g. rhodium there can be mentioned, for example, organic rhodium complexes with ethylene, propylene and the like as well as with bis-olefins, e.g. (Z,Z)-1,5-cyclooctadiene, 1,5-hexadiene, bicyclo[2.2.1]-hepta-2,5-diene or with other dienes which form readily soluble complexes with rhodium. Preferred compounds which yield rhodium are e.g. di-μ-chloro-bis[η⁴-(Z,Z)-1,5-cyclooctadiene]dirhodium(I), di-μ-chloro-bis[η⁴-norbornadiene]dirhodium(I), bis[η⁴-(Z,Z)-1,5-cyclooctadiene]rhodium tetrafluoroborate or bis[η⁴-(Z,Z)-cyclooctadiene]rhodium perchlorate. Di-μ-chloro-bis-[η⁴-(Z,Z)-1,5-cyclooctadiene]diiridum(I) can be mentioned, for example, as a compound which yields iridium.

The ruthenium complexes in question can be represented by the following formula $Ru(Z)_2L$ <span></span> V wherein Z is halogen or A—COO; A is lower alkyl, aryl, halogenated lower alkyl or halogenated aryl; and L is a chiral diphosphine ligand of formula I.

These complexes can be produced, in principle, in a manner known per se. It is convenient and preferred to produce ruthenium complexes by, for example, reacting a complex of the formula

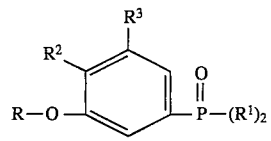 VI wherein $Z^1$ is halogen or $A^1$—COO; $A^1$ is lower alkyl or halogenated lower alkyl; $L^1$ is a neutral ligand, m is the number 1, 2 or 3; n is the number 1 or 2; and p is the number 0 or 1, with a chiral diphosphine ligand of formula I or by reacting a ruthenium complex of the formula $Ru(CF_3COO)_2L$ <span></span> VII wherein L is a chiral diphosphine ligand of formula I, with a salt which yields the anion Z, wherein Z above.

The term "neutral ligand" signifies in the scope of the present invention any conventional readily exchangeable ligand such as, for example, a diolefin, e.g. norbornadiene, (Z,Z)- -1,5-cyclooctadiene etc., or also a nitrile such as aceto- nitrile, benzonitrile and the like. Where m is the number 2 or 3, the ligands can be the same or different.

The ruthenium complexes of formula VI, which are used as starting materials, are known substances or analogues of known substances which can be obtained readily in a manner analogous to the preparation of the known substances, for example according to Albers, M. O. et al., J. Organomet. Chem. 272, C62–C66, (1984).

The reaction of a ruthenium complex of formula VI with a chiral diphosphine ligand of formula I can be carried out in a manner known per se. This reaction can be conveniently effected in an inert organic solvent. As examples of such solvents there can be mentioned e.g. ethers such as tetrahydrofuran or dioxan, ketones such as, for example, acetone, lower alcohols such as, for example, methanol, ethanol etc., halogenated hydrocarbons such as methylene chloride, chloroform and the like or also mixtures of such solvents. Moreover, the reaction can be effected at a temperature between about 0° C. and about 100° C., preferably between about 15° C. and about 60° C., but with the strict exclusion of oxygen.

The reaction of a ruthenium complex of formula VII (obtainable from a complex of formula VI) with a salt which yields the anion Z can be effected in a manner known per se. The term "a salt which yields the anion Z" signifies in the scope of the present invention, for example, ammonium salts, alkali metal salts or other suitable metal salts. In order to improve the solubility of such salts, crown ethers or the like can also be added in certain cases.

The ruthenium complexes of formula V can, moreover, also be produced by reacting a compound of the formula $(L^2 Ru Cl_2)_2$ <span></span> VIII wherein $L^2$ is an aromatic moiety;
with a chiral ligand of formula I. The thus-obtained complexes of the formula $(L^2 Ru L Cl)^+Cl^-$ <span></span> IX wherein L and L² are as above,
can be converted into the complexes of formula V by reaction with a salt which yields the anion Z, wherein Z has the above significance.

The term "aromatic" designates any conventional aromatic moiety particularly benzene, toluene and the like or, preferably, cymene.

The reaction of a compound of formula VIII with a chiral ligand of formula I can be carried out in an analogous manner to the reaction of a compound of formula VI with a chiral ligand of formula I. Preferred solvents in this case are lower alcohols, especially methanol, and the reaction temperature preferably lies at about 40°–50° C. The reaction of a thus-obtained compound of formula IX with a salt which yields the anion Z can also be effected in an analogous manner to the reaction of a compound of formula VII with such a salt which yields the anion Z.

In the complexes of formula IX the anion Cl⁻ can, if desired, be replaced in a manner known per se by a different anion X⁻ such as, for example, $BF_4^-$, $PF_6^-$, $ClO_4^-$ etc. Furthermore, a complex of formula IX can also be converted by reaction with a silver salt of a previously mentioned anion in the presence of a coordinating solvent such as e.g. acetonitrile into a complex of the formula

[L²Ru L S]²⁺2X⁻   X wherein L and L² are as above; X⁻ is a non-coordinating anion; and S is a coordinating solvent.

This conversion can be effected in a manner known per se.

Those complexes of formula V in which Z represents halogen can also be obtained by reacting a complex of the formula

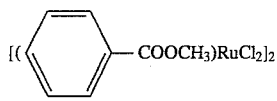   XI with a chiral ligand of formula I.

As mentioned previously, the phosphorus compounds in accordance with the invention in the form of complexes with metals of Group VIII, and especially ruthenium, can be used, inter alia, for asymmetric hydrogenations. As especially suitable substrates there can be mentioned in this connection particularly allyl alcohols such as e.g. geraniol, 6,7-dihydrogeraniol, 6,7-dihydrofarnesol, 6,7,10,11-tetrahydrofarnesol and the like as well as β-keto esters such as e.g. methyl acetoacetate or ethyl acetoacetate etc.

In carrying out such hydrogenations, these complexes can firstly be produced and then added to a solution of the substance to be hydrogenated. Alternatively, they can, however, also be produced in situ, e.g. in the presence of a substance to be hydrogenated.

The asymmetric hydrogenation can be effected in a suitable organic solvent which is inert under the reaction conditions. As such solvents there can be mentioned especially lower alcohols such as e.g. methanol or ethanol or mixtures of such alcohols with halogenated hydrocarbons such as methylene chloride, chloroform and the like or with cyclic ethers such as tetrahydrofuran or dioxan.

The ratio of ruthenium to ligand L conveniently lies between about 0.5 and about 2 mol, preferably at about 1 mol, of ruthenium per mol of ligand. The ratio of ruthenium in the complexes of formula V to the substances to be hydrogenated conveniently lies between about 0.0005 and about 1 mol %, preferably between about 0.002 and about 0.1 mol %.

The asymmetric hydrogenation with the complexes of formula V is conveniently effected at a temperature of about 0° C. to about 100° C. depending on the substrate which is used. This hydrogenation is also conveniently effected under pressure, preferably at a pressure of about 5 to about 200 bar, particularly of about 30 to about 100 bar.

Furthermore, as mentioned earlier, the aforementioned catalysts can be used for enantioselective hydrogen displacements in prochiral allylic systems. In particular, they are interesting e.g. in connection with the preparation of optically active compounds of the general formula

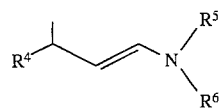   XII wherein R⁴ is protected hydroxymethyl or a residue of the formula

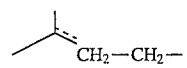

or

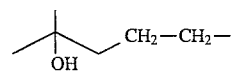

wherein the dotted line can be an additional bond; and R⁵ and R⁶ are lower alkyl containing from 1 to 7 carbon atoms starting from compounds of the general formula

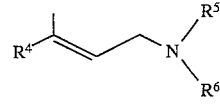   XIII wherein R⁴, R⁵ and R⁶ are as above.

The compounds XII and, respectively, the aldehydes obtained therefrom by hydrolysis as well as the acids and alcohols which are derived from the latter are e.g. of interest as intermediates in the synthesis of the side-chains of vitamins E and K₁.

For the performance of the aforementioned hydrogen displacements, the phosphorus compounds of formula I can be brought into contact as such, in a solution of the compound to be treated, with a compound which yields e.g. rhodium or iridium. Alternatively, the phosphorus compounds of formula I can firstly be reacted in a suitable solvent with a compound which yields e.g. rhodium or iridium to give the corresponding catalyst complex and this can then be added to a solution of a compound to be treated, whereby the latter method is preferred.

Not only the reaction of the phosphorus compounds of formula I with a compound which yields e.g. rhodium or iridium, but also the aforementioned hydrogen displacements can be carried out in suitable organic solvents which are inert under the reaction conditions. As such there can be mentioned especially lower al kanols such as e.g. methanol or ethanol, aromatic hydrocarbons such as benzene or toluene, cyclic ethers such as tetrahydrofuran or dioxan, esters such as e.g. ethyl acetate or also mixtures thereof, and the like. Furthermore, the complex formations can also be carried out in an aqueous medium or in dichloromethane.

The ratio between e.g. rhodium or iridium and the ligands of formula I conveniently lies between about 0.05 and about 5 mol, preferably between about 0.5 and about 2 mol, of metal per mol of ligand of formula I.

The amount of metal in the complexes with the ligands of formula I, based on the compounds to be treated, conveniently lies between about 0.005 and about 0.5 mol %, preferably between about 0.01 and about 0.2 mol %.

The aforementioned hydrogen displacements using metal complexes with the ligands of formula I can be carried out conveniently in an inert organic solvent and at a temperature of about room temperature to about 130° C. This reaction is preferably effected at an elevated temperature, i.e. depending on the solvent which is used either at the reflux temperature of the reaction mixture or in a sealed vessel under pressure.

The following Examples serve to illustrate the invention and are not in any manner a limitation. In these Examples the abbreviations selected have the following significance:

GC: gas chromatography

MeOBIPHEPO: (6,6'-dimethoxybiphenyl-2,2'-diyl)bis-(diphenylphosphine oxide).

DBT: O,O'-dibenzoyltartaric acid.

TLC: thin-layer chromatography.

MeOBIPHEP: (6,6'-dimethoxybiphenyl-2,2'-diyl)bis-(diphenylphosphine).

COD: (Z,Z)-1,5-cyclooctadiene.

DTT: 0,0'-di-p-toluoyltartaric acid.

Tol-MeOBIPHEP: (6,6'-dimethoxybiphenyl-2,2'-diyl)bis(di-p-tolylphosphine).

(MeO)$_2$BIPHEP: (5,5',6,6'-tetramethoxybiphenyl-2,2'-diyl) bis(diphenylphosphine).

(MeO)$_3$BIPHEP: (4,4',5,5',6,6'-hexamethoxybiphenyl-2, 2'-diyl)bis(diphenylphosphine).

EXAMPLE 1 a) 113 g (0.260 mol) of (2-iodo-3-methoxyphenyl)-diphenylphosphine oxide and 49.5 g of iodine-activated copper powder were placed under argon in a 1.5 l four-necked sulphonation flask equipped with a condenser, thermometer, stirrer and headpiece for inert gasification and 500 ml of dimethylformamide were allowed to flow in. The dark brown suspension was heated to 140° C. (oil bath temperature) for 1 hour, after which time complete reaction had occurred according to TLC analysis. The cooled reaction mixture was transferred into a 2 l round flask with 500 ml of methylene chloride and evaporated at 70° C. on a rotary evaporator. The solid dark residue was subsequently treated with 500 ml of methylene chloride, the mixture was boiled for a short time and, after cooling to room temperature, excess copper powder and copper iodide which had formed were filtered off. The filter residue was rinsed with 250 ml of methylene chloride. The filtrate was washed twice with 250 ml of saturated NH$_4$Cl solution, dried over about 100 g of magnesium sulphate, filtered and evaporated. The solid residue (89 g) was stirred with 500 ml of hexane, the mixture was boiled for a short time and decanted while hot. This procedure was repeated 3 times with in each case 500 ml, i.e. a total of 1.5 l, of hexane. The solid residue was dried at 70° C. in a high vacuum, whereafter there were obtained 79.8 g of (RS)-(6,6'-dimethoxybiphenyl-2,2'-diyl)bis(diphenylphosphine oxide) as a light brownish crystallizate. M.p. 307°–308° C. According to NMR this material still contained 0.73 mol equivalents of methylene chloride (corresponding to 9.2 wt. %). The calculated chemical yield was accordingly 90.7%.

ba) 79.5 g of (RS)-MeOBIPHEPO were treated with 440 ml of methylene chloride in a 1.5 l four-necked sulphonation flask equipped with a condenser, mechanical stirrer and thermometer and the mixture was heated to reflux until a clear solution had resulted (about 2 hours). A solution, heated to 50° C., of 56.3 g (0.157 mol) of (–)-O,O'-dibenzoyl-L-tartaric acid in 520 ml of ethyl acetate was poured into the hot solution while stirring vigorously, whereby crystallization occurred immediately after completion of the addition. The reaction mixture was stirred in a cooled oil bath for a further 3 hours. The crystalline material was filtered off under suction and washed with a mixture of 2200 ml of methylene chloride and 260 ml of ethyl acetate. The mother liquor and wash solution of the crystallization were set aside. The crystalline material was dried at 80° C./15 mbar for 4 hours, whereby there were obtained 46.0 g of (R)-MeOBIPHEPO/(–)-DBT adduct as a white crystallizate; m.p. 209°–210° C.; yield 80.1% of theory; $[\alpha]_D^{20}$=+19.2° (c=0.8, ethanol).

bb) The material obtained according to ba) was stirred with 500 ml of methylene chloride and 200 ml of 2N sodium hydroxide solution in a 2 l Erlenmeyer flask using a magnetic stirring rod until all of the solid had passed into solution (30 min.). The phases were separated and the organic phase was washed with 200 ml of 2N sodium hydroxide solution and with 2×250 ml of deionized water, dried over about 50 g of magnesium sulphate, filtered and evaporated. The solid residue was triturated with 250 ml of hot hexane, filtered off under suction after cooling to room temperature and washed with 100 ml of hexane. After drying at 80° C./15 mbar for 4 hours there were obtained 28.4 g of (R)-MeOBIPHEPO as a white crystallizate of m.p. 337.7° C. (thermoanalysis); yield 78.7% of theory based on (RS)-MeOBIPHEPO used; $[\alpha]_D^{20}$=+129.9° (c=1, CHCl$_3$).

bc) The mother liquor and wash solution from ba) were evaporated in a 0.75 l four-necked sulphonation flask equipped with a condenser, dropping funnel and mechanical stirrer. The solid residue was stirred with a mixture of 250 ml of 2N sodium hydroxide solution and 750 ml of methylene chloride for 30 min. The organic phase was washed with 250 ml of 2N sodium hydroxide solution and 3 times with 250 ml of deionized water, dried over about 50 g of magnesium sulphate, filtered and concentrated on a rotary evaporator. The solid residue was dissolved in a sulphonation flask with 250 ml of methylene chloride at the boiling temperature (1 hour). A solution, heated to 50° C., of 28.8 g (0.08 mol) of (+)-O,O'-dibenzoyl-D-tartaric acid in 275 ml of ethyl acetate was poured into the hot solution while stirring vigorously, whereby crystallization occurred immediately. The mixture was stirred in a cold oil bath overnight. The crystalline material was filtered off under suction and washed with a mixture of 90 ml of methylene chloride and 110 ml of ethyl acetate. After drying for 1 hour at 100° C./15 mbar there were obtained 51 g of (S)-MeOBIPHEPO/(+)-DBT adduct as a white crystallizate of m.p. 211°–212° C.; yield 89.6% of theory based on (RS) -MeOBIPHEPO used; $[\alpha]_D^{20}$=–19.4° (c=1, C$_2$H$_5$OH). This material was processed in the same manner as described in paragraph bb) hereinbefore. There were thus obtained 31.8 g of (S)-MeOBIPHEPO as a white crystallizate of m.p. 336.5° C. (thermoanalysis); yield 88.4% of theory based on (RS)-MeOBIPHEPO used; $[\alpha]_D^{20}$ 130.4° (c=1, CHCl$_3$).

ca) 27.9 g of (R)-MeOBIPHEPO were placed in a 0.75 l four-necked sulphonation flask equipped with a condenser, thermometer, mechanical stirrer and 0.25 l dropping funnel and the apparatus was placed under argon by 3-fold evacuation/filling. Then, while stirring well, there were allowed to flow in in succession 95 ml (0.40 mol) of tributylamine, 300 ml of a mixture of xylene isomers and 26 ml of trichlorosilane (34.9 g; 25.7 mmol). The milky-white suspension was boiled at reflux for 3 hours, whereby the progress of the reduction was followed by TLC. The clear solution obtained was cooled to 0° C. (ice/ethanol bath) and 200 ml of 30% sodium hydroxide solution were added dropwise while stirring well in such a manner that the temperature in the reaction vessel did not exceed 70° C. The resulting milky-white mixture was treated with 100 ml of methylene chloride and stirred at 60° C. until two clear separate phases had resulted (1 hour). The aqueous phase was removed by means of a syringe and the organic phase was treated again with 200 ml of 30% sodium hydroxide solution and stirred well at 60° C. After removing the aqueous phase the organic phase was transferred with 100 ml of methylene chloride into a separating funnel, washed three times with 200 ml of deionized water and with 200 ml of saturated NaCl solution, dried over about 50 g of magnesium sulphate, filtered and evaporated on a rotary evaporator, firstly at 40° C. and then at 60° C., and finally evaporated to dryness in a high vacuum at 80° C. The solid residue was suspended in 250 ml of ethanol, heated to 80° C. for a short time and cooled to 0° C. The crystalline material was filtered off under suction, washed with 250 ml of ethanol and with 100 ml of pentane and dried for 1 hour at 100° C./15 mbar. There were obtained 25.75 g of (R)-MeOBIPHEP as a white powder of m.p. 214°–215° C.; yield 97.3%; $[\alpha]_D^{20}$= +42.4° (c=1, CHCl$_3$).

This material was dissolved under argon in 80 ml of toluene (oil bath temp. 110° C.) and the hot solution was treated with 100 ml of ethanol. The mixture was left to cool to room temperature overnight while stirring. The crystallizate was filtered off under suction and washed firstly with a mixture of 80 ml of toluene and 100 ml of ethanol and then with 100 ml of pentane. After drying for 2 hours in a high vacuum at 110° C. there were obtained 22.8 g of (R)-MeOBIPHEP as a white crystallizate of m.p. 214°–215° C.; yield 86.2%; $[\alpha]_D^{20}$=+42.3° (c=1, CHCl$_3$).

cb) 31.5 g of (S)-MeOBIPHEPO (51.25 mmol) were reduced as described under paragraph ca). After working-up there were obtained 29.3 g of (S)-MeOBIPHEP as a white powder of m.p. 214°–215° C.; yield 98.1%; $[\alpha]_D^{20}$=–41.7° (c=1, CHCl$_3$).

Recrystallization of this material as described under ca) yielded 25.1 g of (S)-MeOBIPHEP as a white crystallizate of m.p. 214°–215° C.; yield 84.2%; $[\alpha]_D^{20}$= –42.5° (c=1, CHCl$_3$).

d) The (2-iodo-3-metho xyphenyl)-diphenylphosphine oxide used as the starting material was prepared as follows:

da) 21.4 g (30 ml; 0.211 mol) of diisopropylamine and 170 ml of dry tetrahydrofuran were allowed to flow under argon into a 0.35 l four-necked sulphonation flask equipped with a thermometer, dropping funnel, stirrer and headpiece for a inert gasification. After cooling to –78° C. (dry ice/acetone bath) there were added dropwise within 15 minutes 113 ml (0.186 mol) of 1.65N butyllithium solution in hexane. The cooling bath was removed and the reaction mixture was stirred for a further 20 minutes, whereby the temperature rose to –40° C. Subsequently, the mixture was again cooled to –78° C.

db) 52.5 g (0.170 mol) of (m-metho xyphenyl)-diphenylphosphine oxide were placed in a 1.5 l four-necked sulphonation flask as described under da) and the apparatus was placed under argon by 3-fold evacuation/filling. Then, 350 ml of dry tetrahydrofuran were allowed to flow in and the solution was cooled to –78° C. 313 ml (0.186 mol) of the lithium diisopropylamide solution prepared under da) were added dropwise within 20 minutes while stirring well, with the temperature being held at ≦–70° C. The reaction mixture became reddish-brown in colour at the beginning of the addition and formed a beige suspension towards the end of the addition. After an additional period of stirring of 15 minutes at –78° C. a solution of 47.4 g of iodine in 170 ml of tetrahydrofuran was added dropwise to the solution within 20 minutes, with the reaction mixture being held at ≦–70° C. (The iodine solution had been prepared previously in a separate 250 ml Schlenk tube under argon and had been transferred into the dropping funnel via a steel cannula). Towards the end of the addition there resulted a red solution and there set in the formation of a reddish-brown viscous material which settled on the walls and on the bottom of the reaction vessel. At this point the mechanical stirrer was shut off, the cooling bath was removed and the reaction mixture was left to warm. At about –30° C. there again resulted a clear red solution, the stirring operation was resumed and the mixture was allowed to warm to 0° C. The reaction solution was treated at 0° C. with a solution of 12 g of sodium thiosulphate pentahydrate in 100 ml of deionized water, the mixture was stirred well and the phases were separated. The now yellowish organic phase was washed three times with 200 ml of saturated NaCl solution, dried over about 50 g of magnesium sulphate, filtered and concentrated to dryness on a rotary. evaporator at 40° C. The brown residue was treated with 300 ml of tert.-butyl methyl ether and the mixture was boiled at reflux, whereby the product began to crystallize out. After standing overnight at room temperature the beige crystallizate was filtered off under suction, washed with 100 ml of tert.-butyl methyl ether and dried for 1 hour in a high vacuum at 70° C. There were obtained 55.7 g of (2-iodo-3-metho xyphenyl)diphenylphosphine oxide as a beige powder of m.p. 186°–189° C.

EXAMPLE 2

The following compounds were prepared in an analogous manner to Example 1:

a) (RS)-(5,5',6,6'-Tetramethoxybiphenyl-2,2'-diyl)bis-(diphenylphosphine oxide); m.p. 169°–170° C. (from ethyl acetate), ba) (S)-(5,5',6,6'-tetramethoxybiphenyl-2,2'diyl)bis(diphenylphosphine oxide)/(–)-DBT adduct; (crystallization from chloroform/ethanol); $[\alpha]_D^{20}$=–75° (c=1, CH$_3$OH), bb) (S)-(5,5',6,6'-tetramethoxybiphenyl-2,2'-diyl)bisdiphenylphosphine oxide; m.p. 140°–150° C.; $[\alpha]_D^{20}$=–21.3° (c=1, CHCl$_3$); m.p. 167°–169° C. (from methylene chloride/ethyl acetate/hexane), bc) (R)-(5,5',6,6'-tetramethoxybiphenyl-2,2'-diyl)bis(diphenylphosphine oxide; m.p. 140°–150° C.; $[\alpha]_D^{20}$= +20.6° (c=1, CHCl$_3$), ca) (R)-(5,5',6,6'-tetramethoxybiphenyl-2,2'-diyl)bis(diphenylphosphine); m.p. 171°–172° C.; $[\alpha]_D^{20}$=+5.8° (c=1, CHCl$_3$), cb) (S)-(5,5',6,6'-tetramethoxyphenyl-2,2'-diyl)bis(diphenylphosphine); m.p. 171°–172° C.; $[\alpha]_D^{20}$=–5.8° (c=1, CHCl$_3$).

d) The (2-iodo-3,4-dimetho zyphenyl)diphenylphosphine oxide used as the starting material in this Example was prepared as follows:

da) 75 g of 3,4-dimethoxyphenyl-diphenylphosphine were taken up in 300 ml of methanol. 29.3 ml of 35% H$_2$O$_2$ solution were added dropwise to the suspension while cooling with an ice bath. The clear yellow solution was stirred at room temperature overnight, then treated with 100 ml of sat. Na$_2$SO$_3$ solution and 30 ml of 1N HCl and stirred for a further 1 hour. The resulting suspension was treated with 150 ml of water and the solution was evaporated on a rotary evaporator in order to remove the majority of the methanol. The precipitated yellow crystals were filtered off under suction, taken up in $CH_2Cl_2$, the solution was dried over $MgSO_4$, filtered and evaporated. The residue was dissolved in 450 ml of hot ethyl acetate and the solution was treated with 450 ml of hexane. After standing overnight the crystallizate was filtered off under suction, washed with a small amount of hexane and dried at 0.1 mbar. There were obtained 54 g of (3,4-dimethoxyphenyl)diphenylphosphine oxide as a light beige powder. M.p. 154.5°–156° C.

db) 3.38 g (10 mmol) of (3,4-dimethoxyphenyl)diphenylphosphine oxide and 50 ml of dry tetrahydrofuran were placed in a 0.3 l four-necked sulphonation flask provided with a stirrer, thermometer, dropping funnel and argon gasification. In a separate Schlenk tube 8.0 ml of 1.6N butyllithium solution in hexane (12.8 mmol) were added dropwise under argon and while stirring at −78° C. to a solution of 1.57 g (15.5 mmol) of diisopropylamine in 10 ml of tetrahydrofuran and the solution was stirred at 0° C. for a further 10 minutes. The thus-prepared lithium diisopropylamide solution was then transferred into the dropping funnel of the reaction apparatus and then added dropwise at about −75° C. to the (3,4-dimethoxyphenyl)-diphenylphosphine oxide solution. The resulting pink suspension was stirred at −78° C. for a further 2 hours. Then, it was treated dropwise at <−70° C. with a solution of 3.3 g (13 mmol) of iodine in 20 ml of tetrahydrofuran. Towards the end of the addition there formed a viscous paste which was difficult to stir and which again dissolved when subsequently left to warm to room temperature. The reaction solution was washed 3 times with 20 ml of saturated $Na_2S_2O_3$ solution each time and once with saturated NaCl solution, dried over $Na_2SO_4$, filtered and evaporated. The residue (5 g) was chromatographed on 200 g of silica gel with ethyl acetate and the resulting product was recrystallized from tert.-butyl methyl ether. There were obtained 3.8 g of (2-iodo-3,4-dimethoxyphenyl)-diphenylphosphine oxide as a light beige crystallizate : m.p. 178.5°–179.5° C.

EXAMPLE 3

The following compounds were prepared in an analogous manner to Example 1:
a)  (RS)-(6,6'-Dimethoxybiphenyl-2,2'-diyl)bis(di-p-tolylphosphine oxide); m.p. 299°–300° C.,
ba)  (R)-(6,6'-dimethoxybiphenyl-2,2'-diyl)bis(di-p-tolylphosphine oxide)/(−)-DTT adduct; crystallization from acetone/$CH_2Cl_2$,
bb)  (R)-(6,6'-dimethoxybiphenyl-2,2'-diyl)bis(di-p-tolylphosphine oxide); $[\alpha]_D^{20}=+117°$ (c=1, $CHCl_3$),
bc)  (S)-(6,6'-dimethoxybiphenyl-2,2'-diyl)bis(di-p-tolylphosphine oxide)/(−)-DTT/adduct: this adduct was obtained through direct crystallization from the mother liquor of ba) from acetone/$CH_2Cl_2$,
bd)  (S)-(6,6'-dimethoxybiphenyl-2,2'-diyl)bis(di-p-tolylphosphine oxide); $[\alpha]_D^{20}=-112°$ (c=1, $CHCl_3$),
ca)  (R)-(6,6'-dimethoxybiphenyl-2,2'-diyl)bis(di-p-tolylphosphine); m.p. 209°–210° C.; $[\alpha]_D^{20}=+32.3°$ (c=0.8, $CHCl_3$),
cb)  (S)-(6,6'-dimethoxybiphenyl-2,2,'-diyl)bis(di-p-tolylphosphine); m.p. 208°–209° C.; $[\alpha]_D^{20}=+32.3°$ (c=0.8, $CHCl_3$).

d) The (2-iodo-3-methoxyphenyl)-di-p-tolylphosphine oxide used as the starting material in this Example was prepared as follows:

da) 7.56 g (0.31 mol) of magnesium shavings and 300 ml of dry THF were placed under argon in a 1.5 l sulphonation flask having a mechanical stirrer and 64.0 g (0.342 mol) of 3-bromoanisole were added dropwise within 1 hour, whereby the temperature rose to 35° C. After an additional period of stirring of 1.5 hours, the mixture was cooled using a $CO_2$/acetone bath and a solution of 107.4 g (0.622 mol) of diethyl chlorophosphate in 120 ml of THF was added dropwise within 1 hour, with the temperature being held at <−50° C. The reaction mixture was stirred at −70° C. for 1 hour, then in a melting ice bath at 0° C. for several hours and finally at RT overnight. For the working-up, the mixture was diluted with ethyl acetate, washed 4 times with sat. $NaHCO_3$ solution and once with sat. NaCl solution, dried over $Na_2SO_4$, filtered and concentrated. The resulting oil (75 g) was distilled over a 10 cm Widmer column, whereby 50.9 g of diethyl 3-methoxyphenylphosphate were obtained as a pale yellowish oil. M.p. 118°–120° C./0.1 mbar.

db) 8.35 g (0.345 mol) of magnesium shavings and 50 ml of dry THF were placed under argon in a 0.5 l sulphonation flask. Thereto there was added dropwise within 1.5 hours a solution of 59.0 g (0.345 mol) of p-bromotoluene in 150 ml of THF, whereby the reaction temperature was held at 30°–35° C. by occassional cooling (ice bath). Subsequently, a solution of 28.0 g (0.114 mol) of diethyl 3-methoxyphenylphosphate in 30 ml of THF was added at RT and the reaction mixture was boiled under reflux for 8 hours. For the working-up, the mixture was treated with sat. $NH_4Cl$ solution, extracted with ethyl acetate, the combined extracts were washed with sat. $NaHCO_3$ solution and sat. NaCl solution, dried over $Na_2SO_4$, filtered and evaporated. The yellow oil obtained was crystallized from 200 ml of ether while stirring. The crystallizate was filtered off under suction, washed with ether and dried at 50° C. and 0.1 mbar. There were obtained 22.5 g of (3-methoxyphenyl)-di-p-tolylphosphine oxide as a white powder. M.p. 96°–98° C.

dc) 16.8 g (50 mmol) of (3-methoxyphenyl)-di-p-tolylphosphine oxide were dissolved in 100 ml of dry THF in a 1 l four-necked sulphonation flask provided with a stirrer, dropping funnel, thermometer and argon gasification. In a separate Schlenk tube 34.0 ml of 1.6N n-butyllithium solution in hexane (54.4 mmol) were added dropwise under argon and while stirring at −78° C. to a solution of 9.98 g (70.6 mmol) of 2,2,6,6-tetramethylpiperidine in 50 ml of THF. The solution was warmed to 0° C. for a short period, then again cooled to −78° C. and then added dropwise via a canula at ≦−70° C. to the solution of the phosphine oxide in THF. The resulting red-brown solution was stirred at −78° C. for a further 30 minutes and then treated dropwise with a solution of 15.0 g (59.1 mmol) of iodine in 50 ml of THF, whereby a beige precipitate formed. The reaction mixture was left to warm to 0° C., treated with aqueous sodium pyrosulphite solution and extracted with ethyl acetate. The extracts were washed with sat. $NaHCO_3$ solution and sat. NaCl solution, dried over $Na_2SO_4$, filtered and evaporated. The residue was chromatographed on silica gel (200 g, ethyl acetate), whereby 15.3 g of (2-iodo-3-methoxyphenyl)-di-p-tolylphosphine oxide were obtained. After recrystallization from t-butyl methyl ether there was obtained a white powder with a m.p. of 146°–148° C.

EXAMPLE 4

The following compounds were prepared in an analogous manner to Example 1:
a)  (RS)-4,4',5,5',6,6'-Hexamethoxybiphenyl-2,2'-diyl)bis-(diphenylphosphine oxide); m.p. >250° C., ba) (R)-4,4',5,5',6,6'-hexamethoxybiphenyl-2,2'-diyl)bis-(diphenylphospine oxide)/(−)-DBT adduct; (crystallization from $CH_2Cl_2$/isopropanol); $[\alpha]_D^{20}= +34.1°$ (c=1, $CHCl_3$), bb) (R)-(4,4',5,5',6,6'-hexamethoxybiphenyl-2,2'-diyl)bis-(diphenylphosphine oxide); m.p. 284° C.; $[\alpha]_D^{20}=+51°$ (c=1, $CHCl_3$), bc) (S)-(4,4',5,5',6,6'-hexamethoxybiphenyl-2,2'-diyl)bis-(diphenylphosphine oxide)/(+)-DBT adduct, bd) (S)-(4,4',5,5',6,6'-hexamethoxybiphenyl-2,2'-diyl)bis-(diphenylphosphine oxide); m.p. 284° C.; $[\alpha]_D^{20}=-51.5°$ (c=1, $CHCl_3$), ca) (R)-(4,4',5,5',6,6'hexamethoxybiphenyl-2,2'-diyl)bis(diphenylphosphine); m.p. 238° C. $[\alpha]_D^{20}=-2.4°$ (c=1, $CHCl_3$), cb) (S)-(4,4',5,5',6,6'-hexamethoxybiphenyl-2,2'-diyl)bis-(diphenylphosphine); m.p. 243° C.; $[\alpha]_D^{20}=+2.7°$ (c=1.4, $CHCl_3$).

EXAMPLE 5

By reducing (RS)-(6,6'-dimethoxybiphenyl-2,2'-diyl)bis-(diphenylphosphine oxide), (RS)-(5,5',6,6'-tetramethoxybiphenyl-2,2'-diyl)bis(diphenylphosphine oxide), (RS)-(6,6'-dimethoxybiphenyl-2,2'-diyl)bis(di-p-tolylphosphine oxide) and (RS)-4,4',5,5',6,6'-hexamethoxybiphenyl-2,2'-diyl)bis-(diphenylphosphine oxide) in an analogous manner to Example 1 ca) there were obtained:

(RS)-(6,6'-Dimethoxybiphenyl-2,2'-diyl)bis(diphenylphosphine), m.p. 218°–219° C., (RS)-(5,5',6,6'-tetramethoxybiphenyl-2,2-diyl)bis(diphenylphosphine), m.p. 217°–219° C., (RS)-(6,6'-dimethoxybiphenyl-2,2'-diyl)bis(di-p-tolylphosphine), m.p. 247°–249° C., and, respectively, (RS)-(4,4',5,5',6,6'-hexamethoxybiphenyl-2,2,'-diyl)bis-(diphenylphosphine), m.p. 234.5° C.

EXAMPLE 6

A 500 ml autoclave was charged in a glove box ($O_2$ content <1 ppm) with 24.0 g (155.6 mmol) of geraniol [(E)-3,7-dimethyl-2,6-octadien-1-ol], 1200 ml of methanol and 2.9 mg of Ru[(R)-MeOBIPHEP]$(CF_3COO)_2$ as the catalyst. The hydrogenation was effected at 20° C. and 60 bar. The conversion after 6 hours amounted to 99.9%. The hydrogenation solution was evaporated at 45° C./17 mbar and the crude product was distilled at 60°–65° C./0.03 mbar. There were obtained 23.7 g of (S)-citronellol [(S)-3,7-dimethyl-6-octen-1-ol] as a colourless oil; e.e. 98.9%.

For the e.e. determination, a sample was esterified with (R)-6-methoxy-2,5,7,8-tetramethylchromane-2-carboxylic acid and the mixture of diastereomers was analyzed by gas chromatography on a capillary column.

The Ru[(R)-MeOBIPHEP] $(CF_3COO)_2$ used as the catalyst was produced as follows:

A solution of 8.9 g (27.86 mmol) of (COD)Ru(2-methylallyl)$_2$ in 90 ml of diethyl ether was treated dropwise with 4.3 ml (56.2 mmol) of trifluoroacetic acid. After stirring at room temperature for 1 hour the solvent was removed and the residue was washed twice at −5° C. with 5 ml of diethyl ether. The yellow powder obtained was dried at 0.1 mbar. There were obtained 11 g of [(COD)Ru$(CF_3COO)_2$]$_2$.

$C_{24}H_{24}F_{12}O_8Ru_2$ (870.54) Calc.: C 33.11 H 2.78 F 26.19 Found: C 33.23 H 2.86 F 25.68

0.379 g (0.435 mmol) of this material and 0.507 g (0.87 mmol) of (R)-MeOBIPHEP were treated with 8 ml of diethyl ether/THF (3:1 v/v) and stirred at 40° C. for 16 hours. Thereafter, the solvent was removed and the yellow-orange residue was washed twice with 5 ml of pentane each time. After drying at 0.1 mbar there was obtained 0.76 g of Ru[(R)-MeOBIPHEP] $(CF_3COO)_2$ as a yellow powder.

$^{31}$P-NMR(202.46 MHz):58.47(s)

EXAMPLE 7

A 500 ml autoclave was charged in a glove box ($O_2$ content <1 ppm) with 24.0 g (155.6 mmol) of geraniol, 122 ml of methanol and 20.8 mg (0.026 mmol) of Ru$(CH_3COO)_2$[(R)-MeOBIPHEP] as the catalyst. The hydrogenation was effected at 20° C. and 60 bar. The conversion after 5 hours amounted to 99.9%. The hydrogenation solution was evaporated at 45° C./17 mbar and the crude product was distilled at 60°–65° C./0.03 mbar. There were obtained 23.5 g of (S)-citronellol as a colourless oil; e.e. 98.8%.

For the e.e. determination, a sample was esterified with (R)-6-methoxy-2,5,7,8-tetramethylchromane-2-carboxylic acid and the mixture of diasteromers was analyzed on a OV 1 capillary column.

The Ru$(CH_3COO)_2$[(R)-MeOBIPHEP] used as the catalyst was prepared as follows from the Ru$(CF_3COO)_2$[(R)-MeOBIPHEP used in Example 6:

A suspension of 0.480 g (0.53 mmol) of Ru$(CF_3COO)_2$[(R)-MeOBIPHEP] in 5 ml of methanol was treated with 0.440 g (5.36 mmol) of sodium acetate and stirred at 40° C. for 2 hours. After removing the solvent the residue was dried at 0.1 mbar and subsequently added to a frit. The product was extracted with 15 ml of $CH_2Cl_2$, thereafter the solvent was removed and the residue was triturated with 5 ml of pentane. The supernatant solution was pipetted off and the powder remaining was dried in a vacuum. There was obtained 0.415 g of Ru$(CH_3COO)_2$[(R)MeOBIPHEP].

$^{31}$P-NMR ($CDCl_3$, 202.46 MHz): 63.63 (s).

As an alternative to the foregoing, the catalyst used can be prepared as follows:

A suspension of 2.58 g (2.9 mmol) [(COD)$_2$Ru$_2(CF_3COO)_4$] ($H_2O$) in 20 ml of methanol was stirred at 40° C. for 1 hour with 2.38 g (29.0 mmol) of sodium acetate. After removing the solvent the residue was dried at 0.1 mbar and subsequently added to a frit. The product was extracted with 15 ml of $CH_2Cl_2$, thereafter the solvent was removed and the residue was washed twice with 5 ml of pentane/diethyl ether (5/1 v/v) each time. The yellow solid remaining was dried in a vacuum. There were obtained 1.24 g of (COD)Ru$(CH_3COO)_2$.

$C_{12}H_{18}O_4RU$ (327.34): Calc.: C 44.03 H 5.54 Found: C 43.90 H 5.73.

0.296 mg (0.90 mmol) of (COD)Ru$(CH_3COO)_2$ and 0.522 g (0.90 mmol) of (R)-MeOBIPHEP were placed in 12 ml of ethanol/THF (3/1 v/v) and stirred at 45° C. for 5 hours. The clear red-brown solution obtained was evaporated in a vacuum and the residue was washed 3 times with 10 ml of pentane each time while stirring. After drying in a vacuum there was obtained 0.682 g (94.9%) of Ru$(CH_3COO)_2$[(R)-MeOBIPHEP].

In a further alternative, the catalyst used can be prepared as follows:

A solution of 2.22 g (6.23 mmol) of ($\eta^6$-p-cymene)Ru$(CH_3COO)_2$ (prepared according to D. A. Tocher et al., J. Chem. Soc., Dalton Trans. 1983, 1571–1581, by reacting [(p-cymene)RuCl$_2$] with AgO$_2$CCH$_3$ in toluene) and 3.62 g (6.21 mmol) of [(R)-MeOBIPHEP] in 25 ml of $CH_2Cl_2$ was stirred at 50° C. for 48 hours. Subsequently, the mixture was filtered over a frit and the clear solution obtained was evaporated to dryness. The residue was triturated with 25 ml of pentane, filtered off and washed twice with 20 ml of pentane each time. After drying in a vacuum there were obtained 4.68 g (93.9%) of Ru (CH$_3$COO)$_2$[(R)-MeOBIPHEP].

EXAMPLE 8

A 500 ml autoclave was charged in a glove box (O$_2$ content <1 ppm) with 24.0 g (155.6 mmol) of geraniol and 20 ml of methanol. To this solution was added a catalyst solution prepared by dissolving 5.6 mg (0.0064 mmol) of [Ru(COD)(CF$_3$COO)$_2$]$_2$ and 8.3 mg (0.0129 mmol) of (S)-(MeO)$_2$BIPHEP in 100 ml of methanol at room temperature and stirring for 16 hours. The hydrogenation was effected at 20° C. and 60 bar. The conversion after 1 hour amounted to 99.9%. The hydrogenation solution was evaporated at 45° C./17 mbar and the crude product was distilled at 60°–65° C./0.03 mbar. There were obtained 26.8 g of (R)-citronellol as a colourless oil, e.e. 98.0%.

For the e.e. determination. ea sample was esterified with (S)-6-methoxy-2,5,7,8-tetramethylchromane-2-carboxylic acid and the mixture of diastereomers was analyzed by gas chromatography on a OV 1 capillary column.

EXAMPLE 9

A 500 ml autoclave was charged in a glove box (O$_2$ content <1 ppm) with 27.0 g (175.0 mmol) of geraniol, 136 ml of methanol and 3.38 mg of Ru(CF$_3$COO)$_2$[(R)-Tol-MeOBIPHEP] as the catalyst. The hydrogenation was effected at 20° C. and 60 bar. The conversion after 5 hours amounted to 100.0%. The hydrogenation solution was evaporated at 45° C./17 mbar and the crude product was distilled at 60°–65° C./0.03 mbar. There were obtained 26.7 g of (S)-citronellol as a colourless oil; e.e. 99.3%.

For the e.e. determination, a sample was esterified with (R)-6-methoxy-2,5,7,8-tetramethylchromane- 2-carboxylic acid and the mixture of diastereomers was analyzed by gas chromatography on a OV 1 capillary column.

The Ru(CF$_3$COO)$_2$[(R)-Tol-MeOBIPHEP] used as catalyst was prepared in an analogous manner to that described in Example 6.

EXAMPLE 10

A 500 ml autoclave was charged in a glove box (O$_2$ content <1 ppm) with 27.0 g (175.0 mmol) of geraniol and 36 ml of methanol. To this solution was added a catalyst solution prepared by dissolving 6.35 mg (0.0073 mmol) of [Ru(COD)(CF$_3$COO)$_2$]$_2$ and 10.25 mg (0.0146 mmol) of (S)-(MeO)$_3$BIPHEP in 100 ml of methanol at room temperature and while stirring for 16 hours. The hydrogenation was effected at 20° C. and 60 bar. The conversion after 1 hour amounted to 100.0%. The hydrogenation solution was evaporated at 45° C./17 mbar and the crude product was distilled at 60°–65° C./0.03 mbar. There were obtained 26.8 g of (R)-citronellol as a colourless oil; e.e. 98.8%.

For the e.e. determination, a sample was esterified with (S)-6-methoxy-2,5,7,8-tetramethylchromane-2-carboxylic acid and the mixture of diastereomers was analyzed by gas chromatography on a OV 1 capillary column.

EXAMPLE 11

A 500 ml autoclave was charged in a glove box (O$_2$ content <1 ppm) with 27.0 g (175.0 mmol) of geraniol, 136 ml of methanol and 3.6 mg of Ru(CF$_3$COO)$_2$[(S)-(MeO)$_3$BIPHEP] as the catalyst. The hydrogenation was effected at 20° C. and 60 bar. The conversion after 23 hours amounted to 89.4%. The hydrogenation solution was evaporated at 45° C./17 mbar and the crude product was distilled at 60°–65° C./0.03 mbar. There were obtained 26.4 g of (R)-citronellol, which still contained 10.6% of unreacted geraniol, as a colourless oil; e.e. 98.9%.

For the e.e. determination, a sample was esterified with (S)-6-methoxy-2,5,7,8-tetramethylchromane-2-carboxylic acid and the mixture of diastereomers was analyzed by gas chromatography on a OV 1 capillary column.

The Ru(CF$_3$COO)$_2$[(S)-(MeO)$_3$BIPHEP] used as catalyst was prepared in an analogous manner to that described in Example 6.

EXAMPLE 12

A 500 ml autoclave was charged in a glove box (O$_2$ content <1 ppm) with 33.0 g (145.7 mmol) of (2E,7R)-tetrahydrofarnesol, 170 ml of methanol and 2.65 mg (0.0029 mmol) of Ru[(S)-MeOBIPHEP] (CF$_3$COO)$_2$ as the catalyst. The hydrogenation was effected at 20° C. and 60 bar. The conversion after 2 hours amounted to 99.9%. The hydrogenation solution was evaporated at 45° C./17 mbar and the crude product was distilled at 92°–93° C./0.01 mbar. There were obtained 32.7 g of (3R,7R)-hexahydrofarnesol as a colourless oil; 98.7% e.e. at C(3).

For the e.e. determination, a sample was esterified with (R)-6-methoxy-2,5,7,8-tetramethylchromane-2-carbozylic acid and the mixture of diastereomers was analyzed by gas chromatography on a capillary column.

The Ru(CF$_3$COO)$_2$[(S)-MeOBIPHEP] used as the catalyst was prepared in an analogous manner to Example 6.

EXAMPLE 13

A 500 ml autoclave was charged in a glove box (O$_2$ content <1 ppm) with 46.2 g (180 mmol) of methyl 3-oxotetradecanoate, 131 ml of methanol and a solution of 2.1 mg (0.0036 mmol) of (R)-MeOBIPHEP and 1.08 mg (0.0018 mmol) of Ru$_2$Cl$_4$(COD)$_2$(CH$_3$CN) [Lit.: E. Singleton et al., S. Afr. Tydskr. Chem. 40, 183 (1987)] in 5 ml of dichloromethane. The hydrogenation was effected at 80° C. and 35 bar. The conversion amounted to >99% after 19 hours. The hydrogenation solution was concentrated at 50° C./17 mbar and the crystalline residue was taken up in 500 ml of diethyl ether. In order to separate the catalyst, the ethereal solution was filtered over 100 g of silica gel; e.e.=97.1%. After concentrating and drying the filtered ethereal phase there were obtained 45.8 g of methyl (R)-3-hydroxytetradecanoate as white crystals; e.e.=97.1%. After recrystallization from n-hexane there were obtained 41.9 g of pure methyl (R)-3-hydroxytetradecanoate; m.p. 42°–43° C.; e.e. 99.8%; [α]$_D^{20}$: –16.4° (c=3.8, CCl$_4$).

For the e.e. determination, a sample was esterified with (S)-6-methoxy-2,5,7,8-tetramethylchromane-2-carboxylic acid and the diastereomers were analyzed by gas chromatography on a capillary column.

EXAMPLE 14

A mixture of 2.27 g (10.0 mmol) of (Z)-N,N-diethyl-3,7-dimethyl-2,6-octadienylamine, 36 mg (0.041 mmol) of [θ$^4$-(Z,Z)-1,5-cyclooctadiene][(R)-6,6'-dimethoxybiphenyl- 2,2'-diyl)bis(diphenylphosphine)]rhodium(I) tetrafluoroborate and 5 ml of tetrahydrofuran was heated to 85°–90° C. for 16 hours in a sealed tube. The brownish reaction mixture was evaporated and the residue was distilled in a bulb-tube at about 150° C./0.2 mbar, whereby 2.1 g of (1E, 3R)-N,N-diethyl-3,7-dimethyl-1,6-octadienylamine were obtained as a colourless oil. The distillate obtained was diluted with hexane, treated with 5 ml of 50% acetic acid and the mixture was stirred for 1 hour. The phases were separated and the organic phase was washed with water. 1N HCl, saturated $NaHCO_3$ solution and saturated NaCl solution, dried over $Na_2SO_4$, filtered and evaporated. After distillation in a bulb-tube at about 130° C./15 mbar there were obtained 1.38 g (90%) of (R)-citronellal [(R)-3,7-dimethyl-6-octenal] as a colourless liquid.

$[\alpha]_D^{20}$; +19.2° (c=4.6 in $CHCl_3$) : e.e=98%.

The enantiomeric purity of this material was determined in an analogous manner to Example 13 after reduction to the alcohol.

The rhodium complex used as the catalyst was produced as follows:

A mixture of 203 mg (0.50 mmol) of bis[$\eta^4$-(Z,Z)-1,5-cyclooctadiene]rhodium(I) tetrafluoroblorate and 291 mg (0.50 mmol) of (R)-(6,6'-dimethoxybiphenyl-2,2'-diyl)bis-(diphenylphosphine) in 30 ml of tetrahydrofuran was stirred at room temperature overnight, whereby a flocculent orange-coloured precipitate resulted. The mixture was evaporated to dryness in a high vacuum and the residue was stirred with 30 ml of ether, filtered off, washed with a small amount of ether and dried in a high vacuum. There were obtained 357 mg of [$\eta^4$-(Z,Z)-1,5-cyclooctadiene][(R)-6,6'-dimethoxybiphenyl-2,2,'-diyl)bis(diphenylphosphine)] rhodium(I) tetrafluoroborate as an orange powder.

EXAMPLE 15

In an analogous manner to Example 14, (Z)-N,N-diethyl-3,7-dimethyl-2,6-octadienylamine was reacted with [$\eta^4$-(Z,Z)-1,5-cyclooctadiene][(R)-(6,6,'-dimethoxybiphenyl-2,2'-diyl)bis(diphenylphosphine)]rhodium(I) perchlorate at 65° C. for 48 hours. After hydrolysis there was obtained (R)-citronellal in 88% yield as a colourless liquid:

$[\alpha]_D^{20}$=+18.9° (c=5.9, $CHCl_3$); e.e. 98.4%.

The enantiomeric purity of this material was determined in an analogous manner to Example 13.

The rhodium complex used as the catalyst was produced as follows:

By reacting 209 mg (0.50 mmol) of bis[$\eta^4$-(Z,Z)- 1,5-cyclooctadiene]rhodium(I) perchlorate and 291 mg (0.50 mmol) of (R)-(6,6'-dimethoxybiphenyl-2,2,'-diyl)bis(diphenylphosphine) in an analogous manner to Example 14 there were obtained 431 mg of [$\eta^4$-(Z,Z)-1,5-cyclooctadiene][(R)-(6,6'-dimethoxybiphenyl-2,2'-diyl)bis(diphenylphosphine)]rhodium(I) perchlorate as an orange powder.

EXAMPLE 16

A mixture of 11.37 g (50 mmol) of (Z)-N,N-diethyl-3,7-dimethyl-2,6-octadienylamine, 101.5 mg (0.25 mmol) of bis[$\eta^4$-(Z,Z)-1,5-cyclooctadiene]rhodium(I) tetrafluoroborate, 160 mg (0.275 mmol) of (R)-(6,6'-dimethoxybiphenyl-2,2'-diyl)bis(diphenylphosphine) and 25 ml of tetrahydrofuran was heated to 65° C. while stirring for 20 hours. The brownish-red reaction mixture was evaporated and the residue was distilled in a bulb-tube at about 150° C./0.2 mbar, whereby 10.7 g of (1E,3R)-N,N-diethyl-3,7-dimethyl-1,6-octadienylamine were obtained as a light yellowish oil. The distillate was diluted with 20 ml of hexane, treated with 50 ml of 50% acetic acid and the two-phase mixture was stirred vigorously for 1 hour. After working-up in an analogous manner to Example 14 and distillation in a bulb-tube at 140° C./15 mbar there were obtained 7.18 g of (R)-citronellal as a colourless liquid: e.e.=98.6%

$[\alpha]_D^{20}$=+19.2° (c=4.75 in $CHCl_3$).

We claim:

1. A chiral phosphorous compound of the formula:

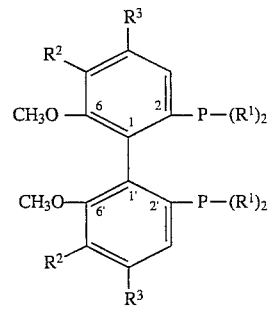

wherein $R^1$ is phenyl or lower alkyl-substituted phenyl, and $R^2$ and $R^3$ are hydrogen or methoxy;
which compound are in the (R)- or (S)-form.

2. The compound of claim 1, wherein $R^1$ is phenyl.

3. The compound of claim 2, wherein the compound has the S configuration.

4. The compound of claim 3, wherein said compound is (S)-(6,6'-dimethoxybiphenyl-2,2'-diyl)-bis(diphenylphosphine).

5. The compound of claim 3, wherein said compound is (S)-(4,4',5,5',6,6'-hexamethoxybiphenyl-2,2-diyl)bis(bis-(diphenylphosphine).

6. The compound of claim 3, wherein said compound is (S)-(5,5',6,6'-tetramethoxybiphenyl-2,2'-diyl)bis(diphenylphosphine).

7. The compound is claim 1, wherein $R^1$ is lower alkyl substituted phenyl.

8. The compound of claim 7, wherein the compound has the S configuration.

9. The compound of claim 8, wherein said compound is (S)-(6,6'-dimethoxybiphenyl-2,2'-diyl)-bis(di-p-tolylphosphine).

10. The compound of claim 2, wherein said compound has the R configuration.

11. The compound of claim 10, wherein said compound is (R)-(6,6'-dimethoxybiphenyl-2,2'-diyl)-bis(diphenylphosphine).

12. The compound of claim 10, wherein said compound is (R)-(5,5',6,6'-Tetramethoxylbiphenyl-2,2'-diyl)bis (diphenylphosphine.

13. The compound of claim 10, wherein said compound is (R)-(4,4',5,5',6,6'-hexamethoxybiphenyl-2,2-diyl)bis-(diphenylphosphine).

14. The compound of claim 7 wherein said compound has the R configuration.

15. The compound of claim 14 wherein said compound is (R)-(6,6'-dimethoxybiphenyl-2,2'-diyl)bis(di-p-tolylphosphine).

* * * * *